US00PP24434P2

(12) United States Plant Patent
van der Sar

(10) Patent No.: US PP24,434 P2
(45) Date of Patent: May 6, 2014

(54) ***HELLEBORUS* PLANT NAMED 'WINTERBELLS'**

(50) Latin Name: ***Helleborus niger*×*Helleborus foetidus***
Varietal Denomination: Winterbells

(75) Inventor: Martinus Willem van der Sar, Maasland (NL)

(73) Assignee: Hilverda Kooij B.V., DeKwakel (NL)

( * ) Notice: Subject to any disclaimer, the term of this patent is extended or adjusted under 35 U.S.C. 154(b) by 72 days.

(21) Appl. No.: 13/373,724

(22) Filed: Nov. 28, 2011

(51) Int. Cl.
*A01H 5/00* (2006.01)

(52) U.S. Cl.
USPC ..... Plt./439

(58) Field of Classification Search
USPC ..... Plt./439
See application file for complete search history.

(56) References Cited

PUBLICATIONS

Grimshaw. Three new hybrid *hellebores*. Plantsman Dec. 2010, pp. 226-231.*

HortiBiz. Elisabeth Sahin baptised new *Helleborus* Jan. 26, 2012, retrieved on Apr. 24, 2013. Retrieved from the Internet at <http://www.hortibiz.com/detail/article/elisabeth-sahin-baptised-new-helleborus/> 2 pp.*

* cited by examiner

*Primary Examiner* — June Hwu
(74) *Attorney, Agent, or Firm* — C. A. Whealy

(57) ABSTRACT

A new and distinct cultivar of *Helleborus* plant named 'Winterbells', characterized by its upright and mounded plant habit; freely branching habit; early and freely flowering habit; long flowering period; single white and light green-colored flowers; and good garden performance.

1 Drawing Sheet

Botanical designation: *Helleborus niger*×*Helleborus foetidus*.
Cultivar denomination: 'WINTERBELLS'.

BACKGROUND OF THE INVENTION

The present invention relates to a new and distinct cultivar of *Helleborus* plant, botanically known as *Helleborus niger*× *Helleborus foetidus*, and hereinafter referred to by the name 'Winterbells'.

The new *Helleborus* plant is a product of a planned breeding program in Honselersdijk, The Netherlands. The objective of the breeding program was to create new early flowering *Helleborus* plants with attractive leaf and flower coloration.

The new *Helleborus* plant originated from a cross-pollination conducted by the Inventor in Honselersdijk, The Netherlands in May, 2004 of a proprietary seedling selection of *Helleborus niger* identified as code number BT7, not patented, as the female, or seed, parent with a proprietary seedling selection of *Helleborus foetidus* identified as code number 1, not patented, as the male, or pollen, parent. The new *Helleborus* plant was discovered and selected by the Inventor as a single flowering plant from within the progeny of the stated cross-pollination grown in a controlled greenhouse environment in Honselersdijk, The Netherlands in February, 2006.

Asexual reproduction of the new *Helleborus* plant by divisions in a controlled greenhouse environment in Honselersdijk, The Netherlands since Mary, 2006, has shown that the unique features of this new *Helleborus* plant are stable and reproduced true to type in successive generations.

SUMMARY OF THE INVENTION

Plants of the new *Helleborus* have not been observed under all possible environmental conditions and cultural practices.

The phenotype may vary somewhat with variations in environmental conditions such as temperature and light intensity without, however, any variance in genotype.

The following traits have been repeatedly observed and are determined to be the unique characteristics of 'Winterbells'. These characteristics in combination distinguish 'Winterbells' as a new and distinct *Helleborus* plant:

1. Upright and mounded plant habit.
2. Freely branching habit.
3. Early and freely flowering habit.
4. Long flowering period.
5. Single white and light green-colored flowers.
6. Good garden performance.

Plants of the new *Helleborus* can be compared to plants of the female parent selection. Plants of the new *Helleborus* differ from plants of the female parent selection in the following characteristics:

1. Plants of the new *Helleborus* flower earlier than plants of the female parent selection.
2. Plants of the new *Helleborus* are more freely flowering than plants of the female parent selection.
3. Plants of the new *Helleborus* have smaller flowers than plants of the female parent selection.
4. Plants of the new *Helleborus* and the female parent selection differ in flower color as plants of the female parent selection have white-colored flowers.
5. Plants of the new *Helleborus* are sterile whereas plants of the female parent selection are fertile.

Plants of the new *Helleborus* can be compared to plants of the male parent selection. Plants of the new *Helleborus* differ from plants of the male parent selection in the following characteristics:

1. Plants of the new *Helleborus* are more freely flowering than plants of the male parent selection.

2. Plants of the new *Helleborus* have larger flowers than plants of the male parent selection.
3. Plants of the new *Helleborus* and the male parent selection differ in flower color as plants of the male parent selection have green-colored flowers.
4. Plants of the new *Helleborus* are sterile whereas plants of the male parent selection are fertile.

Plants of the new *Helleborus* can be compared to plants of *Helleborus niger*×*Helleborus lividus* 'Westerflisk', not patented. In side-by-side comparisons conducted in Honselersdijk, The Netherlands, plants of the new *Helleborus* differed from plants of 'Westerflisk' in the following characteristics:

1. Plants of the new *Helleborus* were more freely branching than plants of 'Westerflisk'.
2. Plants of the new *Helleborus* flowered for a longer period of time than plants of 'Westerflisk'.
3. Plants of the new *Helleborus* had larger flowers than plants of 'Westerflisk'.
4. Plants of the new *Helleborus* and 'Westerflisk' differed in flower color as plants of 'Westerflisk' had green-colored flowers.
5. Plants of the new *Helleborus* were sterile whereas plants of 'Westerflisk' were fertile.

BRIEF DESCRIPTION OF THE PHOTOGRAPH

The accompanying colored photograph illustrates the overall appearance of the new *Helleborus* plant showing the colors as true as it is reasonably possible to obtain in colored reproductions of this type. Colors in the photograph may differ slightly from the color values cited in the detailed botanical description which accurately describe the colors of the new *Helleborus* plant.

The photograph comprises a side perspective view of a typical flowering plant of 'Winterbells' grown in a container.

DETAILED BOTANICAL DESCRIPTION

The aforementioned photograph and following observations, measurements and values describe plants grown in 15-cm containers during the winter in a glass-covered greenhouse in De Kwakel, The Netherlands and under cultural practices which closely approximate commercial *Helleborus* production. During the production of the plants, day temperatures ranged from 12° C. to 16° C. and night temperatures ranged from 4° C. to 10° C. Plants were 23 weeks old when the photographs and the description were taken. In the following description, color references are made to The Royal Horticultural Society Colour Chart, 2007 Edition, except where general terms of ordinary dictionary significance are used.

Botanical classification: *Helleborus niger*×*Helleborus foetidus* 'Winterbells'.

Parentage:

*Female, or seed, parent.*—Proprietary seedling selection of *Helleborus niger* identified as code number BT7, not patented.

*Male, or pollen, parent.*—Proprietary seedling selection of *Helleborus foetidus* identified as code number 1, not patented.

Propagation:

*Type.*—By tissue culture.

*Time to initiate roots.*—About three weeks at 20° C.

*Time to produce a rooted young plant.*—About three months at 20° C.

*Root description.*—Thick, fleshy; white in color.

*Rooting habit.*—Moderately freely branching; medium density.

Plant description:

*Plant form and growth habit.*—Herbaceous perennial; upright and mounding plant habit with flowers held just above and beyond the foliar plane; plant shape is globular; moderately vigorous growth habit.

*Plant height.*—About 32.8 cm.

*Plant diameter* (*area of spread*).—About 47.4 cm.

Foliage description:

*Arrangement.*—Leaves arranged in a basal rosette; leaves palmately compound with five leaflets per leaf.

*Leaf length.*—About 12 cm.

*Leaf width.*—About 12.9 cm.

*Leaflet length.*—About 7.8 cm.

*Leaflet width.*—About 2.9 cm.

*Leaf shape.*—Palmate; orbicular in outline.

*Leaflet shape.*—Elliptic to obovate; lower leaflets occasionally cleft.

*Leaflet apex.*—Acute.

*Leaflet base.*—Attenuate.

*Leaflet margin.*—Serrate.

*Leaflet texture, upper and lower surfaces.*—Smooth, glabrous; leathery.

*Leaflet venation pattern.*—Pinnate.

*Leaflet color.*—Developing leaves, upper surface: Close to N137A. Developing leaves, lower surface: Close to 147B; main veins, close to 187A to 187B. Fully developed leaves, upper surface: Close to N137C; venation, close to 144A. Fully developed leaves, lower surface: Close to 147B; venation, close to 144C to 144D.

*Petiole.*—Length: About 11.5 cm. Diameter: About 4 mm. Texture, upper and lower surfaces: Smooth, glabrous. Color, upper and lower surfaces: Close to 148B, slightly to moderately tinged and dotted with close to 183A to 183C.

Flower description:

*Flower shape and habit.*—Single rotate flowers arranged in terminal and axillary cymes; freely and uniform flowering habit with twelve flowers per inflorescence and about 84 flowers and flower buds developing per plant; flowers facing outwardly to slightly nodding and slightly upright.

*Fragrance.*—None detected.

*Natural flowering season.*—Plants begin flowering about ten months after planting; long flowering period, plants flower from late winter to early spring in The Netherlands.

*Flower longevity on the plant.*—About ten days; flowers not persistent.

*Flower buds.*—Length: About 2.1 cm. Diameter: About 1.1 cm. Shape: Ovate. Color: Close to 145D; base moderately tinged with close to 176B to 176C.

*Inflorescence height.*—About 32.4 cm.

*Inflorescence diameter.*—About 26.6 cm.

*Flower diameter.*—About 4.8 cm.

*Flower depth* (*height*).—About 2.4 cm.

*Petals.*—Transformed into nectaries.

*Sepals.*—Quantity and arrangement: Five arranged in a single whorl. Length: About 3.3 cm. Width: About 2.7 cm. Shape: Broadly elliptic to broadly obovate. Apex: Rounded. Margin: Entire. Texture, upper and lower surfaces: Smooth, glabrous. Color: When opening, upper surface: Close to 154D; towards the margins, close to 157B to 157C; base, close to 144A. When opening, lower surface: Close to 150D and 154D, moderately to strongly tinged with close to 177B and 180B to 180C; base, close to 147B. Fully opened, upper surface: Close to 157D; lower half and base, close to 144A to 144B, slightly tinged with close to 185D; with development, color becoming closer to 144A. Fully opened, lower surface: Close to 154D; towards the margins, close to 157D; moderately tinged with close to 177A to 177B and 184B to 184C; base, close to 146C.

*Peduncles.*—Strength: Moderately strong. Length: About 26.7 cm. Diameter: About 6.5 mm. Aspect: About 50° from vertical. Texture: Smooth, glabrous. Color: Between 183A and 187A moderately tinged and dotted with close to 147D.

*Pedicels.*—Strength: Moderately strong. Length: About 5.6 cm. Diameter: About 2 mm. Aspect: Erect to about 35° from the peduncle axis. Texture: Smooth, glabrous. Color: Close to 151C tinged with close to 176A to 176B.

*Reproductive organs.*—Stamens: Quantity per flower: About 50. Filament length: About 1.4 cm. Filament color: Close to 155C and 157D. Anther shape: Reniform. Anther length: About 2 mm. Anther color: Close to 150B to 150C. Pollen amount: Scarce. Pollen color: Close to 4D. Pistils: Quantity per flower: About five. Pistil length: About 1.1 cm. Stigma shape: Club-shaped. Stigma color: Close to 157D. Style length: About 1 cm. Style color: Close to 147B to 147C. Ovary color: Close to 147B. Nectaries (transformed petals): Quantity per flower: About nine. Length: About 1.1 cm. Diameter, apex: About 2 mm. Diameter, base: About 1 mm. Shape: Flattened triangular. Color: Close to N144A.

*Seeds and fruits.*—Seed and fruit development have not been observed on plants of the new *Helleborus.*

Garden performance: Plants of the new *Helleborus* have been observed to have good garden performance and to tolerate rain and wind. Plants of the new *Helleborus* have been observed to tolerate high temperatures of about 35° C. and are hardy to USDA Hardiness Zone 5.

Pathogen & pest resistance: Plants of the new *Helleborus* have not been shown to be resistant to pathogens and pests common to *Helleborus.*

It is claimed:

1. A new and distinct *Helleborus* plant named 'Winterbells' as illustrated and described.

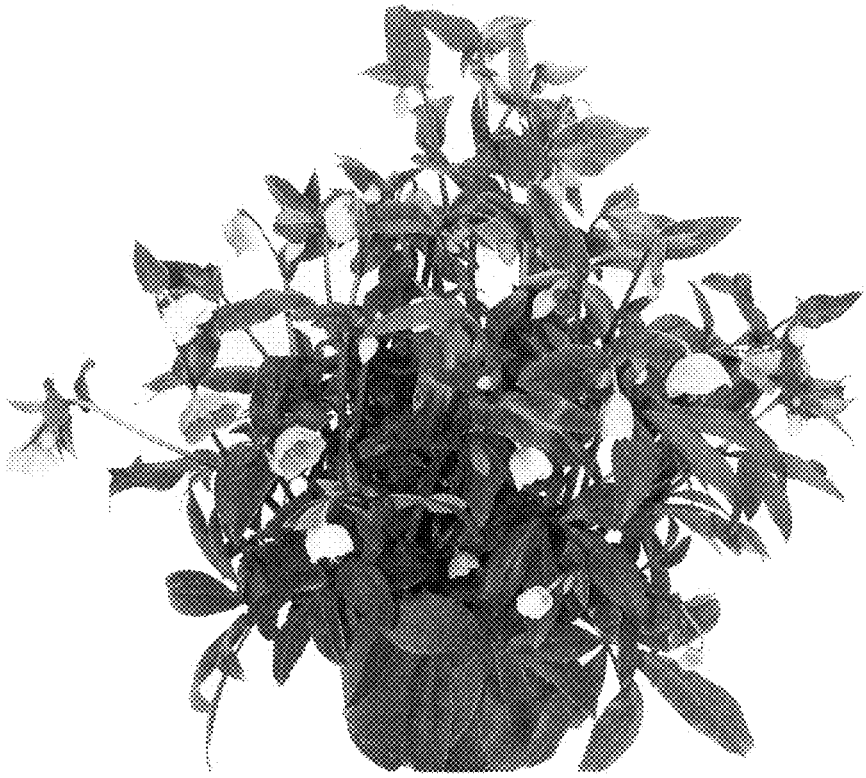

* * * * *